US00PP31919P2

(12) United States Plant Patent
Gielis

(10) Patent No.: US PP31,919 P2
(45) Date of Patent: Jun. 30, 2020

(54) ***SEMPERVIVUM* PLANT NAMED 'BELSEMRED1'**

(50) Latin Name: *Sempervivum arachnoideum*
Varietal Denomination: Belsemred1

(71) Applicant: Belgicactus B.V.B.A., Westerlo (BE)

(72) Inventor: Jef Gielis, Westerlo (BE)

(73) Assignee: BELGICACTUS B.V.B.A., Westerlo (BE)

( * ) Notice: Subject to any disclaimer, the term of this patent is extended or adjusted under 35 U.S.C. 154(b) by 0 days.

(21) Appl. No.: 16/501,779

(22) Filed: Jun. 5, 2019

(51) Int. Cl.
*A01H 5/12* (2018.01)
*A01H 6/32* (2018.01)

(52) U.S. Cl.
USPC ..... Plt./263.1
CPC ..... *A01H 6/32* (2018.05)

(58) Field of Classification Search
USPC ..... Plt./263.1
CPC ..... A01H 6/32
See application file for complete search history.

(56) References Cited

PUBLICATIONS

UPOV hit on *Sempervivum* plant named, 'Belsemred1', QZ PBR 20152893, filed Nov. 28, 2015.*

* cited by examiner

*Primary Examiner* — Anne Marie Grunberg
(74) *Attorney, Agent, or Firm* — Penny J. Aguirre

(57) ABSTRACT

A new cultivar of *Sempervivum* plant named 'Belsemred1' characterized by its foliage that is bright red and turns darker red-purple in autumn and brown to brown-purple in winter, and its rosette-shaped growth habit with new plantlets produced on short runners.

2 Drawing Sheets

Botanical classification: *Sempervivum arachnoideum.*
Variety denomination: 'Belsemred1'.

CROSS REFERENCE TO A RELATED APPLICATION

This application is related to a European plant breeders' rights application filed on Nov. 28, 2015, application No. 2015/2893. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Sempervivum arachnoideum* plant and referred to hereinafter by its cultivar name, 'Belsemred1'. The new cultivar of *Sempervivum* is a hardy succulent perennial grown for use as a landscape and container plant.

The Inventor discovered the new cultivar in 2008 as a naturally occurring branchlet mutation of an unnamed plant of *Sempervivum arachnoideum* that was growing in a container in Westerlo, Belgium.

Asexual propagation of the new cultivar was first accomplished by the Inventor by cuttings in 2011 in Westerlo, Belgium. Asexual propagation by cuttings and offshoots has determined the characteristics to be stable and reproduced true to type in successive generations.

SUMMARY OF THE INVENTION

The following traits have been repeatedly observed and are determined to be the characteristics of the new cultivar.

These attributes in combination distinguish 'Belsemred1' as a unique cultivar of *Sempervivum.*

1. 'Belsemred1' exhibits foliage that is bright red and turns darker red-purple in autumn and brown to brown-purple in winter.
2. 'Belsemred1' exhibits a rosette-shaped growth habit with new plantlets produced on short runners.

The parent plant differs from 'Belsemred1' in having foliage that is green in color. 'Belsemred1' can be most closely compared to the *Sempervivum* cultivars 'Silberkarneol' (not patented) and 'Tordeur's Memory' (not patented). Both are similar to 'Belsemred1' in growth habit and in having red foliage. 'Silberkarneol' differs from 'Belsemred1' in having foliage with red coloration that is less prominent and duller red during the growing season and dull green with dark red to brown hues during the winter, and in having more hairs on the apex of the leaves. 'Tordeur's Memory' differs from 'Belsemred1' in having foliage that loses its red coloration in late summer and autumn and in having larger leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date

BRIEF DESCRIPTION OF THE DRAWINGS

The accompanying colored photographs illustrate the overall appearance and distinct characteristics of 1.5-year-old plants new *Sempervivum* as grown outdoors in 8.5-cm containers in Westerlo, Belgium.

The photograph in FIG. 1 provides a side view of a plant of 'Belsemred1'.

Figure 1:
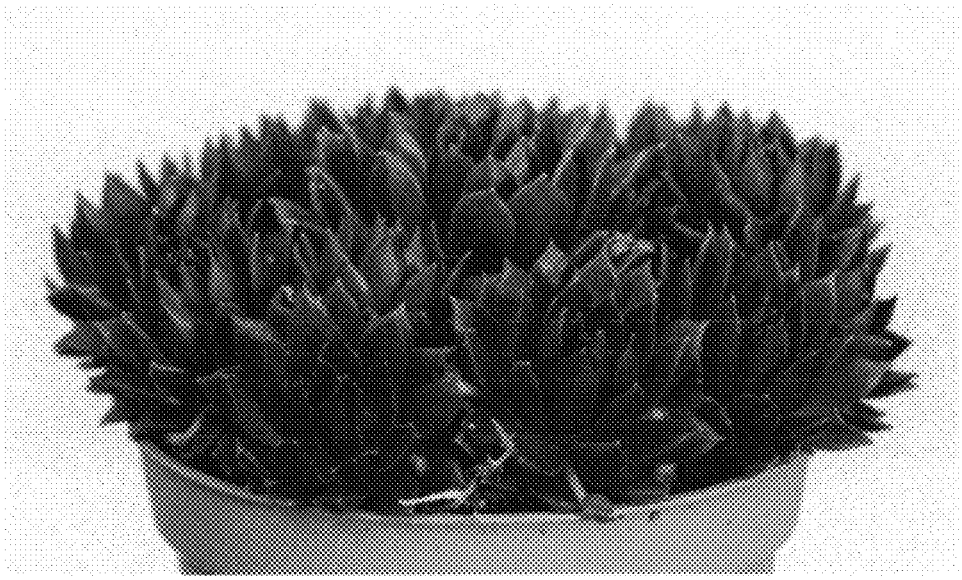
Figure 2:
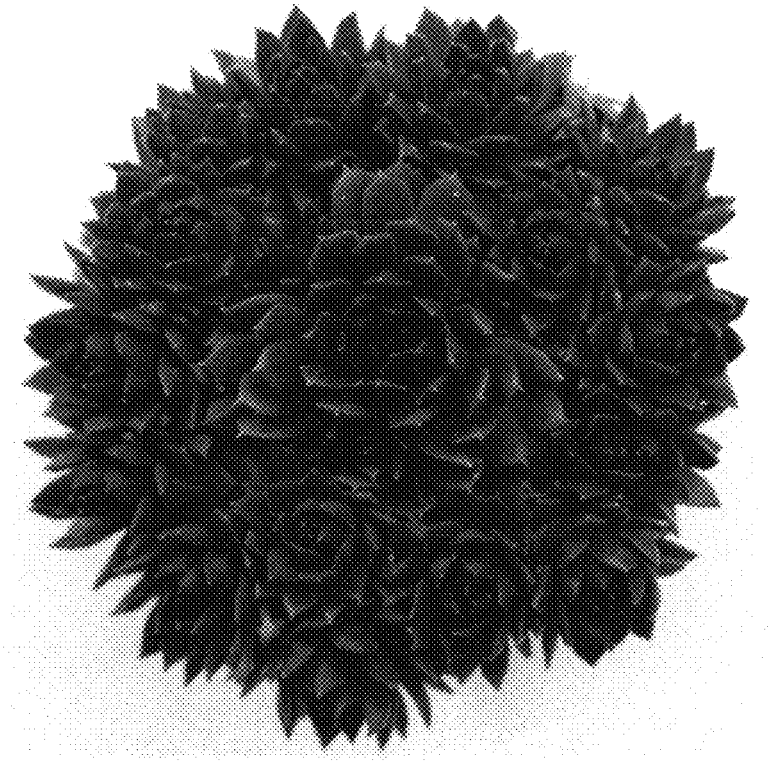

The photograph in FIG. 2 provides a top view of a plant of 'Belsemred1'.

Figure 3:
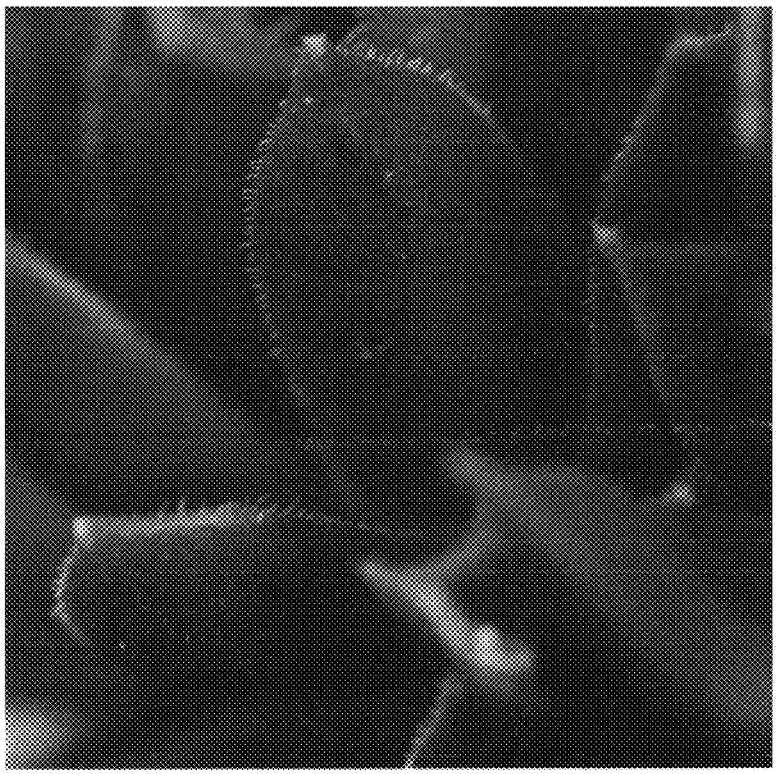

The photograph in FIG. 3 provides a close-up view of the lower surface of the foliage of 'Belsemred1'.

Figure 4:
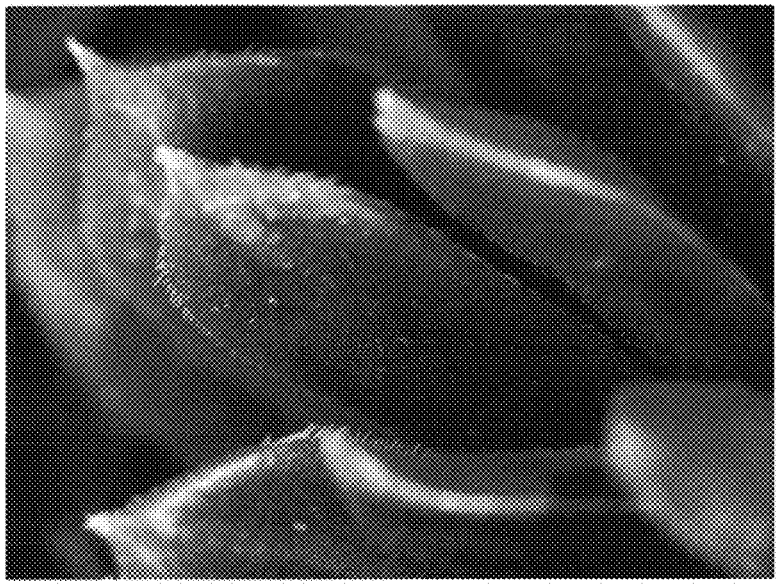

The photograph in FIG. 4 provides a close-up view of the upper surface of the foliage of 'Belsemred1'.

The colors in the photographs may differ slightly from the color values cited in the detailed botanical description, which accurately describe the colors of the new *Sempervivum*.

DETAILED BOTANICAL DESCRIPTION

The following is a detailed description of the new cultivar as observed on 1.5-year-old plants new *Sempervivum* as grown outdoors in 8.5-cm containers in Westerlo, Belgium. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Evergreen succulent perennial.

*Plant habit.*—Basal rosette, offsets clustered around main rosette.

*Height and spread.*—Reaches up to 12 cm in height (without blooms) and 13 cm in spread (with off shoots), average diameter of main rosette is 5.1 cm.

*Hardiness.*—At least hardy in U.S.D.A. Zones 3 to 9.

*Diseases and pests.*—No susceptibility or resistance to diseases or pests has been observed, *Sempervivums* are generally disease free unless grown under wet and cold conditions.

*Root description.*—Rhizomes grow from main rosette and hold offsets, rounded in shape, average of 2.5 cm in length and 1.5 mm in width, texture smooth, glabrous and matte, 200D in color.

*Propagation.*—Cuttings.

*Root development.*—A cutting will root in about 2 months when taking in summer and will fully root in a P9 container in about 6 months from a rooted cutting.

*Growth rate.*—Moderate.

Stem description: Stemless.

Foliage description:

*Leaf shape.*—Oblong, succulent.

*Leaf division.*—Simple.

*Leaf arrangement.*—Rosette.

*Leaf base.*—Broad cuneate.

*Leaf apex.*—Abruptly acute.

*Leaf venation.*—No veins visible.

*Leaf margins.*—Ciliate and un-lobed.

*Leaf attachment.*—Sessile.

*Leaf orientation.*—Flat to slightly curved upward.

*Leaf substance.*—Succulent, average of 3.5 mm in thickness.

*Leaf surface.*—Upper surface glabrous and smooth, lower surface smooth and moderately covered with very short glandular hairs; shorter than 0.1 mm in length, colored white to greyed-white; too small and too sparsely present to be accurately measured with color chart, ciliate margins; an average of 0.2 mm in length, colored white to greyed-white; too small and too sparsely present to be accurately measured with color chart.

*Leaf color.*—Young upper surface; 183A, base; 145B, young lower surface; a color in between 183A and 187B, base 145B to 145C, mature (and autumn) upper surface and lower surfaces 187A, changing towards the base to a color in between 183A and 187B, with very base 146D, color both surfaces in winter; a blend of N200A and 187A.

*Leaf size.*—Average of 2.2 cm in length and 8 mm in width.

Flower description: Flowering is very sparse, not a distinguishing feature as it is grown for its unique foliage, and flowering plants have not been available for data collection.

It is claimed:

1. A new and distinct variety of *Sempervivum* plant named 'Belsemred1' as described and illustrated herein.

* * * * *